United States Patent [19]

Froix

[11] Patent Number: 4,871,785

[45] Date of Patent: Oct. 3, 1989

[54] CLOUDING-RESISTANT CONTACT LENS COMPOSITIONS

[76] Inventor: Michael Froix, 3433 Woodstock La., Mountain View, Calif. 94040

[21] Appl. No.: 156,359

[22] Filed: Feb. 16, 1988

Related U.S. Application Data

[63] Continuation-in-part of Ser. No. 896,603, Aug. 13, 1986.

[51] Int. Cl.[4] .............................................. C08J 00/00
[52] U.S. Cl. ..................................... 523/106; 523/107; 523/108; 526/245; 526/320; 525/327.7; 525/330.1; 525/331.2; 525/342; 525/359.3
[58] Field of Search .................. 523/106, 107, 108; 526/245, 320; 525/327.7, 330.1, 331.2, 342, 359.3

[56] References Cited

U.S. PATENT DOCUMENTS

| | | | |
|---|---|---|---|
| 3,988,274 | 10/1976 | Masahara et al. | 526/320 |
| 4,038,264 | 7/1977 | Rostoker et al. | 526/320 |
| 4,170,582 | 10/1979 | Mori et al. | 526/320 |
| 4,200,563 | 4/1980 | Komiya | 526/320 |
| 4,228,269 | 10/1980 | Loshaek et al. | 526/306 |
| 4,259,467 | 3/1981 | Keogh et al. | 526/279 |
| 4,275,183 | 6/1981 | Kuzma | 526/303 |
| 4,327,202 | 4/1982 | Foley, Jr. | 526/320 |
| 4,351,922 | 9/1982 | Yoshida et al. | 526/320 |
| 4,379,864 | 4/1983 | Gallop et al. | 523/106 |
| 4,405,773 | 9/1983 | Loshaek et al. | 526/317 |
| 4,433,125 | 2/1984 | Ichinohe et al. | 526/279 |
| 4,546,123 | 10/1985 | Schäfer et al. | 526/320 |
| 4,598,122 | 7/1986 | Goldenberg | 525/61 |
| 4,752,627 | 6/1988 | Froix | 523/106 |

FOREIGN PATENT DOCUMENTS

| | | | |
|---|---|---|---|
| 181301 | 10/1984 | Japan | 526/320 |
| 2178435 | 2/1987 | United Kingdom | 526/320 |

OTHER PUBLICATIONS

Macret et al., (1982) Polymer 23:748–753.
Pedley et al., (1980) British Polymer Journal 12:99–110.
Tighe et al., (1976) British Polymer Journal, pp. 71–77.

*Primary Examiner*—Paul R. Michl
*Assistant Examiner*—Patrick A. Doody
*Attorney, Agent, or Firm*—Irell & Manella

[57] ABSTRACT

Contact lens compositions containing monomers or cross-linking materials which result in satisfactory moisture content but lowered protein absorption capability are described. Lenses are comfortable for extended wear, but because of lowered protein absorption do not become opaque, and present less infection risk. Included are compositions with over 20% conventional cross-linkers, with 20–100% cross-linkers which are unsaturated diesters of the alcohol of the formula $HO(CH_2CH_2O)_nH$ wherein n is 5–300; or 1–69% copolymerizing monomer which is an ester of an alcohol of similar formula; or 0.1–90% cross-linkers which are diesters of the diol of the formula $HOCH_2(CF_2)_mCH_2OH$, or which contain silyl components such as $HO(SiR_2O)_x$—; or with inclusions of 1–40% polyethylene glycol or polyethylene oxide; or copolymers containing 1–90% polyethylene oxide segments when the composition does not include carboxylic acids and is not treated with alkali.

8 Claims, No Drawings

CLOUDING-RESISTANT CONTACT LENS COMPOSITIONS

This is a continuation-in-part of U.S. Ser. No. 896,603, filed Aug. 13, 1986.

TECHNICAL FIELD

The invention relates to contact lens compositions. In particular, it concerns contact lenses which exhibit a range of moisture contents and of optical properties, but which uniformly resist the opaqueness which generally occurs as a direct function of moisture content through the absorption of protein from tears.

BACKGROUND ART

The number of publications and patents covering the contact lens art is almost overwhelmingly extensive. Review articles have appeared periodically. For example, see those by Tighe, B. J., *Brit Polymer J* (September 1976) 71–77; Pedley, D. G. et al, Brit Polymer J 23:748–753.

Briefly, and in general, the first contact lenses were glass, but this was replaced in the late 1940's by the so-called "hard" contact lenses made mostly of polymethyl methacrylate The hard plastic lenses have excellent optical characteristics and good machining and polishing qualities, but are practically impermeable to oxygen due to their low moisture content, and they require a thick film of tear between themselves and the eye. A few other hard lens materials now available are somewhat more permeable to oxygen.

Another basic class, the flexible silicone lenses are oxygen permeable but are strongly hydrophobic which renders them uncomfortable and they are furthermore susceptible to discoloration due to absorbed lipids from tear fluid.

A third category, the soft hydrogel contact lenses, were first proposed in 1960 by Wichterle and Lim *Nature* (1960) 185:117. Various compositions based on lenses made of hydrophilic polymeric materials have been the subjects of a number of U.S. and foreign patents.

In general, the hydrogel lenses are addition polymers of acrylic or methyl acrylic acid ester derivatives with alcohols containing hydroxyl groups capable of conferring hydrophilicity. Commonly used materials include 2-hydroxyethyl methacrylate (HEMA), 2,3-dihydroxypropyl methacrylate (DHPM), hydroxyethyl acrylate (HEA); vinyl pyrrolidone (Vp), methacrylic acid (MAA); acrylic acid (AC), methyl methacrylate (MMA), glycerol methacrylate (GMA), and acrylamide (AA). The foregoing list is representative of materials which have been used either alone or in combination as the polymerizing material to form the hydrophilic lens. In addition, the polymers have been cross-linked by the inclusion of the diacrylic esters or dimethacrylic esters of ethylene glycol monomers and polymers, such as ethylene glycol diacrylate (EGDA) and ethylene glycol dimethacrylate (EGDMA) as well as the corresponding acrylates and dimethacrylates of polyethylene glycol (PEGDA and PEGDMA). These cross linkers are generally present in low amounts, approximately 0.1–5%.

In addition, soft but hydrophobic lenses have employed fluoroacrylates (FA) and fluoromethacrylates (FMA) either alone or as copolymers with more hydrophilic monomeric units.

Despite the increased comfort and convenience of soft contact lenses, which permit extended wear due to the ability of the lens to be compatible with the eye and permit the passage of oxygen to the cornea, problems have arisen because the high moisture content of soft lenses is also conducive to the absorption of proteins which in time discolor and obscure the transparency of the lens. The absorption of protein is serious not only because the lens is effectively fogged, but also because it provides a breeding ground for bacteria which can result in severe eye infection. The invention herein provides a solution to this problem by furnishing a range of compositions which, while retaining a high moisture content, substantially reduce protein absorption with its attendant problems.

DISCLOSURE OF THE INVENTION

The invention relates to contact lens compositions which have a range of hydrophilicities but which retain the ability to absorb sufficient amounts of water to provide very satisfactory oxygen permeability Nevertheless,.they withstand the encroachment of the protein components of tears. These compositions may employ conventional polymer materials, such as HEMA and polyvinyl pyrrolidone, but will, in any event, include substantial percentages of hydrophilic cross-linkers with or without hydrophobic components, or copolymerization using monomers which contain polymeric hydrophilic side chains, or block polymers characterized by inclusions of hydrophilic polymers either covalently bound or not.

In general, therefore, the contact lenses and compositions of the invention contain significant amounts of the polyethylene oxide (PEO) unit —$(CH_2CH_2O)_n$— either as part of the copolymer forming the backbone, as side chains to said backbone, as a blend with the polymeric materials, or as a cross linker. In addition, the inclusion of polyfluorinated analogs of the PEO diesters as cross linkers is novel, and can be useful to regulate hydrophilicity.

Accordingly, in one aspect, the invention is directed to contact lens compositions containing a high proportion, i.e., 20–100%, of cross-linker including conventional cross-linkers. The cross-linking material is preferably, however, a hydrophilic diacrylate or dimethacrylate of relatively high molecular weight such as polyethylene glycol diacrylate. The composition may also include hydrophobic cross-linkers which are generally the fluorinated analogs of the PEGDA and PEGDMA diesters.

In another aspect, the invention relates to compositions which contain cross-linking materials not previously used for this purpose. Such materials include hydrophilic unsaturated diesters of polymeric ethylene glycol—i.e. of glycol of the formula $HO(CH_2CH_2O)_nH$, wherein n is 5–300. They also may include fluorinated analogs wherein the glycol has the formula $HOCH_2(CF_2)_mCH_2OH$, wherein m is 1–10. The relative amount of these newly used cross-linking materials is in the range of 0.1–90%.

An additional novel cross-linking material to which the invention is directed is an unsaturated diester of a copolymer of dimethyl siloxane and polyethylene glycol. These copolymers have the formula

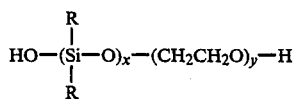

wherein R is lower alkyl (1-5), phenyl, and preferably methyl, x is 1-300 and y is 1-400. These copolymeric cross-linkers can be used in a range of 0.1-90% as cross-linkers in the compositions of the invention.

In still another aspect, the invention is directed to compositions and lenses which contain polymerized ethylene glycol moieties as side chains to the major polymer components. Such compositions can be obtained by including, for example, acrylic or methacrylic monoesters of polyethylene glycol in the preparations. Masuhara et al, U.S. Pat. No. 3,988,274, disclose soft contact lenses having 70-93% by weight of an alkylene glycol unsaturated ester in combination with certain other ingredients wherein the lens is then treated in alkali. These compositions of the invention can contain proportions of the monomer in the backbone of up to only 69%, do not require the additional components which are included in the Masuhara compositions, and do not require treatment with alkali.

In still another aspect, the invention relates to compositions and lenses which are polymerized from blends of conventional or other monomers with 1-40% polyethylene glycol, or the mono- or diesters thereof (with saturated acids) or the mono- or diethers thereof, along with solubilizing amounts of acrylic or methacrylic acid.

In still another aspect, the invention relates to compositions and lenses which are block copolymers of ethylene oxide and unsaturated monomers. These block copolymers contain segments of polymer units formed from the unsaturated monomer units alternating with segments of polyethylene oxide, wherein the PEO segments comprise 1-90% of the copolymer. Several protocols for preparation may be used, including preliminary polymerization of the conventional monoesters of unsaturated acids, followed by addition of ethylene glycol to the blocks with subsequent PEO block formation.

In other aspects, the invention relates to methods to construct contact lenses using the compositions of the invention, and to methods to prevent protein absorption by providing contact lenses of the claimed compositions.

It should further be noted that although the materials and methods disclosed herein are discussed in terms of contact lenses (by far the most important and quantitatively significant application), ocular correction using these materials may also be in the form of intraocular lenses and intracorneal lenses. The general requirements for protein resistance which are useful in contact lens compositions are, of course, equally or more critically important in these applications.

Additionally, it is apparent that protein resistance is a valuable property in any apparatus or device which comes in contact with the metabolism of the human or animal body. Accordingly, the compositions of the invention are useful in the preparation of materials for catheters or for medical tubing of any kind used to carry body fluids or other fluids into and out of the body, sutures, cannulas, surgical prostheses, vascular grafting materials and materials used for reconstruction such as heart valves. These compositions are also useful for apparatus used to store or administer body fluids such as blood bags.

Accordingly, in another aspect, the invention relates to medical devices constructed of the compositions of the invention.

In still another aspect, the invention relates to methods to coat lenses and other medical devices so that they become more protein resistant. Devices and lenses constructed of any polymeric material can be used as substrates for such coating.

MODES OF CARRYING OUT THE INVENTION

The general polymeric backbone of the composition is, in general, provided by the polymerization of conventional monomers such as hydroxyethyl acrylate (HEA), vinyl pyrrolidone (VP), and hydroxyethyl methacrylate (HEMA), and may include a hydrophobic monomer component such as fluoroalkyl acrylate (FAA) or fluoroalkyl methacrylate (FAMA). The hydrophobic component, however, is generally present only as a copolymer and in relatively low percentage. In general, the compositions found in the art contain mainly hydrophilic residues in the major polymer component, although regulation of the hydrophilicity/hydrophobicity balance by inclusion of, for example, FAMA has been disclosed (U.S. Pat. No. 4,433,111).

While the foregoing materials are by far the most common used in manufacture of contact lenses or other devices of medical importance, additional known backbone materials are not excluded from the polymers which provide the backbone component of the compositions of the invention. For example, the use of polysiloxanes and acrylics containing silylated sidechains is also well known in the art. For example, U.S. Pat. No. 4,259,467 incorporated herein by reference discloses contact lens compositions containing polysiloxanes or copolymers of polysiloxanes and acrylates. U.S. Pat. Nos. 4,508,884 and 3,808,178, both incorporated herein by references disclose contact lens compositions containing polymers of acrylic acid as backbone polymers wherein the acrylic acid monomer moieties contain polysilylated sidechains. U.S. Pat. No. 4,433,125 also incorporated herein by reference, describes the use of polyacrylate and methacrylates as backbone polymers wherein the monomeric unites have silylated sidechains which may include fluorosubstituents. All of these silylated polymers may be used as the backbone polymers in the compositions of the herein invention. Indeed, modifications of these materials containing two acrylate moieties rather than only one may be used as cross-linkers in addition to those as described below as part of the present invention.

Not previously disclosed in the art is the inclusion of the monoesters of polymeric ethylene glycol as monomers for the backbone polymers, to obtain compositions which show a high level of resistance to protein absorption. The resultant side chains containing repetition of the —CH$_2$CH$_2$O— or polyethylene oxide (PEO) unit contribute to the ability of the lens to resist the absorption of protein while retaining a satisfactory moisture content. In a modified approach, this PEG component can also be supplied as such in the original blend; it may or may not esterify to free acrylic or methacrylic acid used to solubilize it in the polymerization process. If used in a block copolymer, it forms part of the backbone chain.

As used herein, "PEG unsaturated monoester" refers to moieties of the formula $RO(CH_2CH_2O)_nAc$ wherein R is H or lower alkyl (1–4C), n is 2–300 and Ac is an unsaturated carboxylic acid residue.

The unit may also be supplied in the form of a mono or diether (i.e. as a compound of the formula $RO(CH_2CH_2O)_nR$ wherein each R is typically lower alkyl (1–4C), e.g. methyl, ethyl or n-butyl and one R may be H).

Compositions available in the prior art have included as cross-linking agents, 0.1–5% of an additional hydrophilic diacrylate or dimethacrylate. Thus, compositions used in the art have included, for example, triethylene glycol dimethacrylate (TEGDMA) or ethylene glycol dimethacrylate, generally in percentages lower than 5% relative to the basic polymer.

The compositions of the present invention differ from the art in that (1) they may contain 20%–100% of any unsaturated diester as cross-linking agent; and/or (2) they may include as cross-linking agents fluorinated alkyl unsaturated diesters, such as diacrylate or dimethacrylate, which have not previously been used as cross-linking materials; and/or (3) they may include as cross-linking agents unsaturated diesters of high molecular weight polymeric ethylene glycol; and/or (4) they may include in the major polymer a substantial amount (typically 1–69%) of unsaturated monoesters of high molecular weight polymeric ethylene glycol or its esters which are thus present as side chains or higher amounts of these materials under specified conditions not previously known in the art; and/or (5) they may include in the prepolymerized mixture blends of 1–40% polyethylene glycol or polyethylene oxide (n=5–300) along with sufficient acrylic or methacrylic acid to solubilize the polymers; typically up to 20%; and/or (6) they may be formed as block copolymers of $PEO-(CH_2CH_2O-)_n$ units with unsaturated monomers.

It should be noted that while the compositions of the invention described below are described in terms of the most conventional lens composition ingredients, this is done for convenience in illustration. It should not be interpreted to exclude analogous compositions which employ modifications of these materials. For example, many mono- and diesters of acrylic and methacrylic acid are readily commercially available and relatively inexpensive to prepare; however, the properties provided by the approaches to cross-linking and side chain moieties disclosed herein are equally achievable in compositions where the major polymer component is derived from a butenoic or pentenoic ester, for example. In addition, as noted above, the sidechains may bear silylated groups, and also may be polyfluorinated. Sidechain silylated groups include, for example, groups of complexity such as

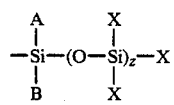

wherein A and B are independently alkyl (1–5), phenyl, are X-substituted silyl groups, and the X-substituted silyl group,

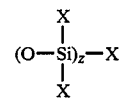

wherein X is alkyl (1–5) or phenyl, and wherein z is 1–5 can also be used. Most commonly used among these is 3-methacryloxypropyl (TRIS) trimethylsiloxylsiloxane (TRIS) used in the illustrations below. This is a compound of the general class

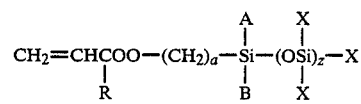

wherein X, A, B and z are as above-defined, R is H or methyl and a is 1–3. For TRIS, R is methyl, a is 3, A and B are trimethylsiloxy and X is methyl. Thus, TRIS has the formula

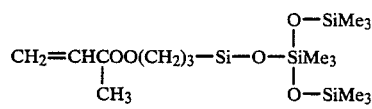

Also useful are unsaturated esters of alcohols with polyfluorinated backbones of the general formula

wherein R is H or methyl, b is 1–5, d is 1–20 and Y is F or H.

Thus, while acrylic acid (AC) and methacrylic acid (MAA) are referred to for convenience throughout, it should be understood that this is not intended to be limiting, and other corresponding unsaturated acids or esters can be used in all cases, including those esterified to complex sidechains.

The foregoing compositions of the invention are particularly useful in the construction of contact lenses and intraocular and intracorneal forms of these lenses. However, they are useful in the construction of biocompatible materials in general. It has long been recognized that the ability to resist protein absorption is highly important with regard to maintaining biocompatibility (Brash, et al, *J Biomed Materials Res* (1985) 19:1017–1029). Not only is protein absorption or adsorption the first event upon contact of a material with, for example, blood, the adsorbed protein later mediates interactions with additional elements in the fluids with which the material comes into contact. Later adhesion of cells to nonphysiologic substrates, for example, is believed to be so mediated (Baier, et al, (ibid), 1157–1167).

Protein adsorption has also been shown to be a precursor to platelet agglomeration on the surfaces of foreign materials in contact with blood. This may account for thrombosis at blood-polymer surfaces, so that reduction of protein adsorption may prevent thrombosis and embolization (Kim, et al, *J Polymer Sci* (1979) 66:429–441).

Thus, in addition to lens materials, the compositions of the invention are useful in construction of a variety of devices which make physiological contact with the body. Included among these are catheters, cannulas, and other surgical prostheses.

PERCENTAGES: DEFINITIONS

The basis of the percentage calculated differs according to what component or substance is being referred to, although all percentages are by weight. As used herein, percentages of cross-linker are expressed by weight using the backbone polymer as a basis. Thus, if the composition contains 4 grams of polymerized HEMA, a composition containing "10% cross-linker" contains 0.4 grams of, for example, polyethylene glycol diacrylate. The corresponding composition containing "100% cross-linker" has 4 grams of this material. Similarly, the percentage of the particular non-conventional, $-(CH_2CH_2O)_n-$, monomer component of the invention expressed as a percentage of the copolymer uses the total backbone copolymer weight (excluding any cross-linker but including the non-conventional component) as a basis. Thus, compositions which are "10%" polyethylene glycol 600 methacrylate in a HEMA polymer contain PEGMA 600:HEMA at a ratio of 10:90 regardless of the amount of cross-linker. This is true of the acrylic/methacrylic acid and PEG/PEO added to the prepolymerization blends—the percentages are based on total polymer weight excluding these blended materials.

However, as further detailed below, the percentage of water in wetted lenses is also expressed by weight, but uses total swollen weight as a basis.

Polymers involving ethylene glycol residues are denoted using conventional terminology wherein the number following the designation refers to the molecular weight of the ethylene glycol polymer component of the substance. Thus, PEGDMA 4000 refers to the diester formed from PEG 4000; the M.W. of the two methacrylic moieties is not included. Since the molecular weight of the repeating unit $(CH_2CH_2O-)$ is 44, an approximation of the number of units can be obtained by dividing by 44, and PEG 4000 contains about 90 subunits.

None of the percentage limits herein should be construed as precise. Numerical limits are placed for definiteness, and represent reasonable approximations. It is, nevertheless, understood that the properties of the compositions as a function of the relative amounts of components represent a continuum, and sharp changes at the designated "boundary" values should not be expected.

MODES OF PREPARATION

In general, the compositions are prepared using conventional polymerization techniques, including UV and peroxide catalyzed polymerizations. The polymerizations are conducted by mixing all of the components of the lens composition and initiating polymerization of the mixture. In an additional protocol, the cross-linking component may be added as a coating to the basic polymer which has been prepolymerized.

In one illustrative procedure, the components are thoroughly mixed (applying heat if necessary to liquefy those materials which are solid at room temperature, such as polyethylene glycol diacrylate 4000 (PEGDA 4000), polyethylene oxide, or polyethylene glycol). This mixture, wherein the components are mixed together "neat", is provided with a small amount of photoinitiator, such as Durocure 1173, and then exposed to UV light for sufficient time to effect the desired polymerization. This is typically about 15 seconds to several minutes.

In the alternative, similar mixtures are polymerized by first degassing and then adding about 0.01%–0.5% of a peroxide or other chemical free radical generator such as benzoyl peroxide or azo(bis)isobutyro nitrile (AIBN). The mixture is then heated in an oven at relatively low temperatures (e.g. 40°–60° C.) for sufficient time to effect polymerization, typically 1–24 hours.

If a material to provide protein resistance is to be coated on a prepolymerized material, this is typically applied as a 1% solution in methanol, although a range of concentrations can be used, as described below. The samples to be coated are pretreated in methanol for a period of 1 day-1 week, and then placed in the 1% methanol solution containing the resistance conferring material (e.g., PEGDA 4000) and an effective amount of photoinitiator, such as Durocure. The samples remain in contact with the coating solution for approximately 1 day, and are then removed and exposed to ultraviolet light for sufficient time to effect chemical binding to the lens, typically 15–90 seconds.

THE PROTEIN RESISTANT PROPERTY

The lenses of the invention, characterized by their water absorbing ability with retention of resistance to protein absorption, are prepared from compositions which contain significant amounts of the repeating polyethylene oxide subunit $-(CH_2CH_2O)_n-$ wherein n is 1–300. This subunit can be provided in several ways. First, unusually high amounts of short chain unsaturated diesters of PEO wherein n is 1–4 can be used as cross-linkers, i.e., at cross-linker concentrations of 20–100%. Second, the cross-linkers can include corresponding diesters wherein n is 5–300. Smaller weight percentages are needed to be effective in this case. The hydrophilicity of such cross-linkers can be offset to any desired extent by inclusion of effective amounts of polyfluorinated diester analogs. Third, the unsaturated esters of the backbone polymer may be the esters of PEO wherein n is 2–300 so that the PEO is effectively a side chain found on the backbone polymer. Again, esters of the fluorinated analog may also be included to regulate hydrophilicity. Fourth, PEO polymers wherein n is 5–300 may be added to the mixture to be polymerized, presumably forming blends which hold the PEO in place non-covalently, or in which the PEO is esterified to one of the polymer-forming units and winds up as a side chain. Finally, ethylene glycol or its oligomers can be used to form block copolymers with other monomeric units.

NEW CROSS-LINKING AGENTS

The invention employs, for the first time, fluorinated diacrylates and dimethacrylates as cross-linking agents. These materials are made from the commercially available fluorinated dialcohols: $HOCH_2(CF_2)_mCH_b$ $_2H$, wherein m is an integer of 1–10. To obtain the diesters, these diols are reacted with appropriate reactive forms of unsaturated acids. The most conventional of these are acryloyl or methacryloyl chlorides. The reaction is conducted in a suitable aprotic solvent, such as toluene. For convenience in obtaining the purified product, an amine, such as trimethylamine is then added to precipitate the resulting HCl as triethylamine hydrochloride. The solution is filtered and the diester, e.g., the fluorodiacrylate or dimethacrylate is distilled to obtain the desired cross-linking substance. Of course, any suitable purification method can be used to recover the desired diester.

In addition to the diesters of fluorinated diols, the unsaturated diesters of ethylene glycol and polyethylene glycol may also be used, either alone, or together with the fluorinated cross-linkers. The acrylate and dimethacrylate diesters of polyethylene glycol are commercially available, however, any desired member of this series can be obtained by reacting the polyethylene glycol (PEG) of the appropriate molecular weight with acryloyl or methacryloyl chlorides or the corresponding acids as described above. The reactive forms of alternative unsaturated acids can also be used.

Diesters of alcohols of the formula $HO(CH_2CH_2O)_nH$, wherein n is 1-4 are conventional in contact lens compositions; however the use of diesters wherein n is 5-300 is not. Typical molecular weights for the PEG diesters used in the invention range up to approximately 13000. Thus, the invention compositions may either contain extraordinarily high amounts of conventional cross-linking diesters of the above diol wherein n is 1-4, or any convenient amount of cross-linker of corresponding formula wherein n is 5-300. The invention encompasses, in general, compositions wherein the percentage of cross-linker, whatever its nature, is in the range of 20-100%. Lower percentages (down to 0.1%) are included in the invention when the cross-linker is unconventional—i.e. the above high molecular weight diol diesters or diesters of the fluorinated diols. The upper limits are approximately the same—about 90-100%.

Another novel class of cross-linkers include the unsaturated diesters of copolymers of diethylsiloxanes and polyethylene glycol. These have the formula

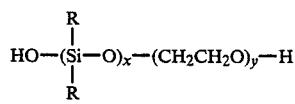

wherein R is alkyl (1-5), phenyl, or, preferably, methyl, x is 1-300 and y is 1-400. These novel cross-linkers can be used alone in a percentage of 0.1-90% of the compositions, or can replace the fluoromethylenediol diesters in admixture with polyethylene glycol diesters per se. The above polydimethyl siloxane/polyethylene glycol (PMS/PEG) copolymer can be used alone as a cross-linker, or in admixture with the unsaturated diester of at least one fluoromethytlene diol (FMD) of the formula $HOCH_2(CF_2)_mCH_2$, OH, wherein m is 1-10, or in admixture with the unsaturated diester of at least one polyethylene glycol (PEG) of the formula $HO(CH_2CH_2O)_nH$, wherein n is 1-300, or in admixture with a mixture of the above FMD and PEG crosslinkers. However, if x is much larger than y, the decreased hydrophilicity may need to be adjusted elsewhere in the composition.

NEW POLYMER COMPONENTS

The water-attractive, but protein repelling properties of the compositions can also be achieved by employing unsaturated monoesters of polyethylene glycol or its ether or ester derivative as components of the major polymer component. These monoesters are prepared in a manner similar to that described for the diesters above, but the stoichiometry of the reactants is controlled so that the monoester is the chief product. It can then be purified from the reaction mixture by standard separation techniques.

The monoester formed from the PEG alcohol, of the formula $HO(CH_2CH_2O)_n R$ wherein R is H, lower alkyl, or saturated acyl, and wherein n is 2-300, is used as 1-69% of the total polymer composition to confer the desired properties. In addition, up to 90% of this 69% upper limit suggested for copolymerized monomer may be the monoester of the generic polyfluorinated diol $HOCH_2(CF_2)_mCH_2OH$, abbreviated herein FAmMA for the methacrylate ester or FAmAC for the acrylate ester. In these compositions, m is 1-10, and the total copolymerized monomer is 69%; therefore if 20% FA$_m$MA, for example, is present, the upper limit for the PEG derived monomer is 49%.

These percentages should not be regarded as precise limits the most effective compositions are those wherein a correct balance is achieved between the value of n and the percentage of the PEG-containing monoester. This relationship is mostly empirical, however, in general, the higher the value of n, the smaller the percentage of copolymer needed, though this is not a linear function.

When substantial percentages of the PEG monoester are used, it is not necessary to treat the lens in alkali in order to achieve an appropriate water content. In particular, the invention includes lenses containing 1-90% in the backbone monomer of an unsaturated monoester of PEG containing 2-300 units of ethylene glycol which have a water content of >40% without alkali treatment. It is also advantageous, in the lenses of the present invention wherein the protein resistant property is conferred by the inclusion of 1-90% PEG unsaturated monoester in the backbone polymer, to exclude free carboxylic acids from the composition. It is recognized that trace amounts of free acid may remain in the monoester preparations used to form the polymer backbone, however, this level is quite low. By compositions which "do not contain free carboxylic acid" is meant those wherein no carboxylic acid component is deliberately added. The trace contaminants may still be present. Accordingly, the lenses and compositions of the invention include those wherein PEG unsaturated monoesters comprise 1-90% of the backbone monomer but contain no carboxylic acids as components.

Preferred compositions containing substantial amounts of the PEG monoester monomer unit in the backbone polymer can be formulated for low, medium, and high water content lenses. For lenses of high water content (~74%) preferred compositions contain 30±10% of the PEG monomer, preferably PEGMA of MW 200-2000, preferably 350-600, most preferably 550. The remainder of the composition may be a mixture of other components, preferably 7.5% HEMA, 36% VP and 27% MMA (all ±5%).

For medium water content lenses (~55%) the same PEG containing monomer percentage and type are preferred; a preferred composition for the remaining components is 30% HEMA, 15% VP and 25% MMA, all ±5%.

For low water content lenses (~43%) the preferred range for the PEG monomer is 35±10%, again preferably PEGMA of MW ranges as stated above. The preferred remaining composition is 45% HEMA, and 20% MMA (both ±5%).

In all cases, cross linking can be effected using, e.g., 0.1-0.5% EGDMA.

An alternate set of preferred compositions for high and medium water content lenses is as follows.

| Medium EWC | Water Content 50-60% |
|---|---|
| HEMA | 45% ± 5% |
| NVP | 5% ± 5% |
| MMA | 20% ± 5% |
| PEGMA (350-5000) | 30% ± 10% |
| EGDMA | 0.1-0.5% |
| High EWC | Water Content 70-80% |
| NVP | 45% ± 5% |
| MMA | 25% ± 5% |
| PEGMA (200-5000) | 30% ± 10% |
| EGDMA | 0.1-0.5 |

BLENDS

Compositions and lenses falling within the scope of the invention and exhibiting the desired properties of ability to absorb water while resisting protein absorption can also be prepared by including in the compositions before polymerization is carried out an effective amount of a $(CH_2CH_2O)_n$ based polymer, in the form of polyethylene glycol (PEG) or polyethylene oxide PEO) wherein n is 5-300. An amount effective to confer the desired properties is about 1-40% of the base polymer weight. (The basic polymer is subject to considerable variation, but includes conventional polymerizing units such as HEMA, VP, and fluorinated monoesters.) It is helpful to include acrylic or methacrylic acids in the blend to help solubilize the PEG or PEO (or mixture thereof). In general, higher percentages of PEG/PEO require larger percentages of the acids—about 20% acid is sufficient to solubilize 40% PEG/PEO. Upon polymerization, these preformed polymers are included in some form in the final lens composition.

BLOCK COPOLYMERS

While copolymers of the unit $(CH_2CH_2O)-n$ and unsaturated materials are known, particularly where the unsaturated material is styrene, these have not been used to construct contact lenses. When the amount and length of the PEO portion is properly chosen, and appropriate unsaturated components are used, these copolymers make excellent lenses with protein resisting properties. In general, the PEO segment will comprise 1-90% of the copolymer, and the value of n will be at least 5, and generally not more than 300, as the PEO may crystallize at high concentration. The unsaturated components will generally be those commonly used in contact lenses (MAA and AC and their esters), although alternatives may be useful. Techniques for formation of such addition copolymers are well known in the art. See, for example, U.S. Pat. No. 2,828,345 and GB Pat. No. 722,746, both describing PEO /styrene; U.S. Pat. No. 3,050,511, and Brooks, T. W., et al, Polymer Prep ACS, Div of Pol p. 796. Polysiloxanes may also be used in the formation of these block copolymers—e.g., part of the copolymer may have the formula $(SiR_2O)_x$— wherein R represents alkyl, fluoroalkyl, phenyl, phenylalkyl fluorophenyl, fluorophenylalkyl and the like.

COATED AND GRAFTED COMPOSITIONS

The lenses and other materials of the invention can also be constructed by coating or grafting the invention compositions or the standard prior art compositions with a protein resistant outer layer. Indeed, a variety of conventional lenses and devices can be so treated. In addition, therefore, to lenses, tubing, prostheses and other devices made from compositions derived by polymerization of unsaturated esters, objects formed from other standard polymers such as polyethylene, polypropylene, polysulfone, PVC, polyurethane, nylon, polyetherimide, polyacrylether ketone, polymethylpentene and the like can be coated according to the invention method.

The materials may be directly coated by treating the uncoated article with a solution of a $(CH_2CH_2O)_n$— containing monomer for example, a 0.1-25% by 0.5-5% weight solution preferably 0.2-10%, and most preferably 0.5-5% solution of unsaturated diester of a polyol such as polyethylene glycol diacrylate (PEGDA) or the monoester of a polyethylene glycol. The coated article is then permitted to dry.

Grafting can be effected by swelling the composition to be grafted with a suitable solvent containing from 0.1-25% by weight, preferably 5-25%, of either or both of an unsaturated monoester or diester derivative of polyethylene glycol. The samples to be grafted are then exposed to a source of radiation such as high intensity ultraviolet or gamma radiation, or thermally grafted with the aid of a free radical catalyst to effect grafting of the polymerizing outer coating to the base composition.

PREFERRED EMBODIMENTS

The following represent illustrative embodiments of the compositions of the invention. As elsewhere herein, the percentage of cross-linking agent is given using the backbone polymer as a base. Table 1 shows such typical preferred compositions.

In Table 1 below, the following abbreviations are used: hydroxyethyl methacrylate (HEMA), triethylene glycol dimethacrylate (TEGDMA), hexafluoropentamethylene diacrylate (HFDMDA), polyethylene glycol diacrylate (PEGDA), polyethylene glycol methacrylate (PEGMA), wherein the molecular weight of the polyethylene glycol component follows. For example, polyethylene glycol (200) diacrylate is abbreviated PEGDA 200 and polyethylene glycol (550) methacrylate is abbreviated PEGMA (550). Further abbreviations include N-vinyl pyrrolidone (VP); hexafluorobutyl methacrylate (HFBMA); hydroxyethyl acrylate (HEA), ethoxyethoxyethyl acrylate (EEEA); hexafluoropentamethylene dimethacrylate (HFPMDA); octafluorohexamethylene diacrylate (OFHMDA); trifluoroethyl methacrylate (TFEMA), methacrylic acid (MAA); methyl methacrylate (MMA); ethylene glycol dimethacrylate (EGDMA); 3-methacryloxypropyl (tris) (trimethylsiloxy) silane (TRIS); isobornyl methacrylate (IBMA); pentadecafluorooctyl methacrylate (PDFOMA); tridecafluorooctyl methacrylate (TDFOMA); diethyleneglycol dimethacrylate (DEGDMA); and azo(bis) isobutyronitrile (AIBN).

TABLE 1

| Backbone Polymer | Cross-Linker | % Cross-Linker |
|---|---|---|
| HEMA | TEGDMA | 10 |
| " | " | 15 |
| " | HFPMDA | 10 |
| " | " | 15 |
| " | PEGDA 200 | 20 |
| " | PEGDA 200 | 20 |
| " | HFPMDA | 2 |
| " | PEGDA 4000 | 20 |
| " | PEGDA 4000 | 20 |
| " | HFPMDA | 4 |
| HEMA:VP, 3:1 | TEGDMA | 10 |
| " | " | 40 |
| " | HFPMDA | 10 |
| " | " | 40 |

TABLE 1-continued

| Backbone Polymer | Cross-Linker | % Cross-Linker |
|---|---|---|
| " | OFHMDA | 15 |
| " | HFBMA | 10 |
| | TEGDMA | 5 |
| " | HFBMA | 10 |
| | HFPMDA | 5 |
| " | PEGDMA 600 | 10 |
| " | " | 20 |
| " | PEGDMA 600 | 20 |
| " | HFPMDA | 2 |
| " | PEGDMA 4,000 | 10 |
| " | " | 100 |
| " | PEGDMA 4,000 | 100 |
| | HFDMDA | 10 |
| " | OFHMDA | 10 |
| HEMA:VP:MAA, 2:1:0.5 | PEGDA 4,000 | 20 |
| " | " | 24 |
| " | PEGDA 4,000 | 20 |
| | HFPMDA | 6 |
| " | TEGDMA | 8 |
| | HFPMDA | 8 |
| HEMA:VP:HEA, 2:1:1 | TEGDMA | 15 |
| " | TEGDMA | 15 |
| | HFPMDA | 5 |

EXAMPLES

The following examples are intended to illustrate but not to limit the invention.

EXAMPLE 1

Determination of Protein

Protein uptake by the polymerized samples was measured using tritiated sample protein solutions. The labeled protein solution contained 1.20 mg/ml lysozyme, 3.88 mg/ml albumin, and 1.60 mg/ml. gamma globulin in pH 7.4 phosphate buffer, a composition roughly mimicking the composition of tears.

The proteins in the test solution had been labeled with tritium using standard reductive methylation techniques with tritiated sodium borohydride, or by esterification of the primary amino groups with tritium-labeled N-succinimidyl propionate. The labeled proteins were then purified by gel chromatography before addition to cold protein to prepare the test solution.

For determination of protein absorption, samples were soaked in distilled water for 1 week and then cut into 1 cm$^2$ portions having a thickness of 0.1–0.2 cm. The 1 cm$^2$ samples were soaked in methanol for 3 days, and then cleaned using ultrasound in methanol solution. The cleaned samples were then soaked in distilled water for 1 week, changing the water each day. The samples were finally removed from the distilled water, and equilibrated in pH 7.4 phosphate buffer solution and then placed in the protein test solution for 24 hours at 37° C.

After exposure to the protein solution, the samples were removed, washed with pH 7.4 phosphate scintillation vial. The vials were heated to 90° C. for 24 hours in 1N nitric acid, then cooled, and scintillation fluid added. Four determinations were made for each lens sample and the results averaged.

EXAMPLE 2

Determination of Moisture Content

The standard measure of moisture, equilibrium water content (EWC) is defined as the weight of water in the lens divided by the total weight of the swollen lens ×100.

To determine this value, dry 1 cm$^2$ samples were weighed, then placed in triple distilled water for 1 week. The swollen samples were then reweighed and the EWC calculated as the difference between dry and wet sample weight divided by the weight of the wet sample×100.

EXAMPLE 3

Comparative EWC and Protein Absorption

The effectiveness of percentages of hydrophilic cross-linker content in maintaining satisfactory EWC while reducing protein absorption is shown in this example. The basic polymer is a copolymer formed from 2.4 g HEMA and 0.60 g VP. The samples were prepared by mixing the monomers of the backbone copolymer along with the designated cross-linking agent, and 3 drops of Durocure 1173. The mixtures were irradiated with UV light (1000 watts) for 90 seconds. Compositions were made which contained the following amounts of the specified cross-linker in addition to 3 g of the monomer mixture:

Composition 1 contains 0.02 g TEGDMA, or 0.67%, as cross-linker. This represents the prior art composition.

Sample 2 contains 0.60 g PEGDA 600, or 20%, as cross-linker.

Compositions 3, 4, 5, and 6 each contained PEGDA 4000 as cross-linker in the amounts of 1.50 g, 0.60 g, 0.30 g, and 0.13 g respectively. Sample 7 contained 1.20 g of TEGDMA as a cross-linker. Table 2 gives the results of EWC and protein determinations of these compositions.

TABLE 2

| Composition | % Cross-linker | EWC | Protein μg/cm$^2$ BSA | IgG | Lysozyme | Total |
|---|---|---|---|---|---|---|
| 1 | 0.67% TEGDMA | 42 | 46.8 | 1.54 | 86.9 | 135.2 |
| 2 | 20% PEGDA 600 | 43 | 47.5 | 1.14 | 5.7 | 54.3 |
| 3 | 50% PEGDA 4000 | 60 | 20.7 | 0.92 | 10.6 | 32.2 |
| 4 | 20% PEGDA 4000 | 56 | 19.5 | 0.88 | 29.1 | 49.5 |
| 5 | 10% PEGDA 4000 | 54 | 28.1 | — | — | — |
| 6 | 4.3% PEGDA 4000 | 53 | 31.6 | — | — | — |
| 7 | 40% TEGDMA | 18 | 29.5 | 1.27 | 5.8 | 36.6 |

The results in Table 2 show that the compositions containing the elevated cross-linker content representative of the compositions of the invention give dramatically lower protein contents than the control. In addition, the water content of the compositions is unaffected, except when high amounts of an extremely low molecular weight cross-linker are used. Without intending to be bound by any particular theory, it would appear that the high percentage of TEGDMA lowers water content by restricting the space in the polymer network. This has a simultaneous effect of lowering the protein absorption capacity. However, it is clear from the results that the desired lower protein absorption can also be obtained in compositions which maintain a high water content. The low percent water content of composition 7 does not, however, render it useless, as this level of hardness may be desirable in the case of some wearers.

of hydrophilic and hydrophobic cross-linking agents in compositions 14 and 15–18. Composition 14 is based on the shorter hydrophilic cross-linker PEGDA 600; compositions 15–18 on the longer PEGDA 4000. The results for these compositions are shown in Table 4.

TABLE 4

| Composition | % Cross-linker | EWC | Protein μg/cm² BSA | IgG | Lysozyme | Total |
|---|---|---|---|---|---|---|
| 1 | 0.67% TEGDMA | 42 | 46.8 | 1.54 | 86.9 | 135.2 |
| 14 | 20% PEGDA 600, 2% HFPMDA | 40 | 44.4 | 1.91 | 4.8 | 51.1 |
| 15 | 20% PEGDA 4000, 2.1% HFPMDA | 50 | 31.1 | 1.36 | 15.5 | 48.0 |
| 16 | 20% PEGDA 4000, 5% HFPMDA | 46 | 16.1 | 0.61 | 13.4 | 30.1 |
| 17 | 20% PEGDA 4000, 10% HFPMDA | 38 | 16.5 | 0.58 | 2.3 | 19.4 |
| 18 | 20% PEGDA 4000, 25% HFPMDA | 25 | — | 0.42 | 3.0 | — |

EXAMPLE 4

Effect of Hydrochobic Cross-Linking Agents

The ability of fluorinated diester cross-linked compositions to resist protein absorption was determined in this Example. Compositions 8–12 contain increasing amounts ranging from 0.67%–40% HFPMDA as cross-linker; composition 13 contains 10% OFHMDA. The results of comparable determinations on these compositions are shown in Table 3.

TABLE 3

| Composition | % Cross-linker | EWC | Protein μg/cm² BSA | IgG | Lysozyme | Total |
|---|---|---|---|---|---|---|
| 1 | 0.67% TEGDMA | 42 | 46.8 | 1.54 | 86.9 | 135.2 |
| 8 | 0.67% HFPMDA | 40 | 43.1 | 1.48 | 65.9 | 110.5 |
| 9 | 2.6% HFPMDA | 39 | 33.1 | 1.64 | 55.8 | 90.5 |
| 10 | 10% HFPMDA | 27 | 22.2 | 1.64 | 15.4 | 39.2 |
| 11 | 20% HFPDMA | 15 | 21.1 | 1.64 | 10.4 | 33.1 |
| 12 | 40% HFPMDA | 12 | 20.0 | 1.78 | 17.5 | 39.5 |
| 13 | 10% OFHMDA | 29 | — | 1.45 | 20.6 | — |

These results show that a dramatic decline in protein absorption can be obtained using approximately of the fluorinated cross-linker. However, this accompanied a diminution in moisture content, and the compositions are therefore used when such a diminution is acceptable. Nevertheless, a decrease in the absorption, in particular, of lysozyme is obtained similar to that obtained using the high molecular weight hydrophilic cross-linking agent of Example 3.

EXAMPLE 5

Hydrophilic/Hydrophobic Cross-Linkers

A balance between water content and protein absorption capacity can be obtained by utilizing a combination It can be seen that by combining a percentage of hydrophobic cross-linker with a hydrophilic one, the water content can be maintained at substantially the level of the compositions of the prior art for soft lenses, while the protein absorption capability is reduced. For example, composition 17 retains substantially the same water content as composition 1 but the protein absorption is cut almost by a factor of 10.

EXAMPLE 6

Effect of Cross-Linking in HEMA-Based Compositions

Results similar to those shown in examples 3, 4, and 5 were also obtained when the basic composition contains polymerized HEMA alone. All of the tested compositions contained 3 g HEMA in addition to varying amounts of hydrophilic and hydrophobic cross-linkers. Compositions 1A and 1B represent prior art compositions used as controls. Results of determinations similar to those above are shown in Table 5 for compositions 19–27.

TABLE 5

| Composition | % Cross-linker | EWC | Protein μg/cm² BSA | IgG | Lysozyme | Total |
|---|---|---|---|---|---|---|
| 1A | None | 49 | 77.4 | 2.55 | 172.1 | 252.1 |
| 1B | 0.67% TEGDMA | 32 | 39.8 | 2.58 | 108.2 | 150.6 |
| 19 | 20% PEGDA200 | 27 | 46.5 | 1.50 | 10.3 | 58.3 |
| 20 | 11% PEGDA4000 | 42 | 42.6 | — | — | — |
| 21 | 20% PEGDA4000 | 43 | 32.8 | 1.48 | 34.2 | 68.5 |
| 22 | 2.67% OFHMDA | 31 | — | 1.71 | 41.2 | — |
| 23 | 15% OFHMDA | 19 | 21.1 | 1.80 | 13.4 | 36.6 |
| 24 | 15% HFDMDA | 19 | 12.5 | 1.64 | 11.5 | 25.6 |
| 25 | 22% PEGDA200, 2.3% HFPMDA | 27 | 36.8 | 1.76 | 17.1 | 55.7 |

TABLE 5-continued

| Composition | % Cross-linker | EWC | Protein μg/cm² BSA | IgG | Lysozyme | Total |
|---|---|---|---|---|---|---|
| 26 | 20% PEGDA4000, 3.3% HFPMDA | 39 | 45.0 | 0.91 | 9.9 | 56.4 |
| 27 | 15% TEGDMA | 23 | 15.4 | 1.52 | 13.3 | 30.2 |

The results for the HEMA based compositions are similar to those for the HEMA/VP copolymers. The absorption of protein can be reduced dramatically simply by increasing the concentration of the conventional cross-linker TEGDMA, but with a concomitant lowering of EWC values. On the other hand, the absorption of protein can be lowered without altering substantially the amount of moisture either by using long chain cross-linkers or by using a combination of hydrophilic and hydrophobic cross-linking materials.

EXAMPLE 7

HEMA/HEA/VP Compositions

A comparison was also run between a composition containing 40:40:20 HEMA:HEA:VP as the basic polymer with and without the addition of 20% PEGDA 4000 as cross-linker. The EWC for both samples was substantially the same (66% for the control and 67% for the cross-linked composition). However, the lysozyme absorbed dropped from 97.9 μg/cm² in the control composition to 47.1 μg/cm² for the cross-linked lens.

EXAMPLE 8

Effect of MAA Addition

Samples containing various amounts of MAA in the basic polymerization unit were also used to determine the result of various cross-linking additions. In one set of compositions the basic polymer contained 1.80 g HEMA, 1.20 g VP, and 0.09 g MAA. The control composition 1C also contained 0.07 g or 2.3% TEGDMA as cross-linker. The results for these compositions (28–30) are shown in Table 6.

tionally contains 0.24 g of TEGDMA, composition 31 contains 0.26 g of HFPMDA. Again the moisture content was not affected, but the absorption of lysozyme was dramatically lowered.

EXAMPLE 9

Effect of Coating Cross-Linker

A lens constructed entirely of 3 g of HEMA was coated with a 1% solution of PEGDA 4000 according to the procedure described hereinabove. The coated lens absorbed only approximately ⅔ of the BSA absorbed by the lens containing HEMA alone. Other parameters were not determined. The HEMA lens absorbed 77.4 μg/cm² of BSA (Composition 1A) while the coated lens absorbed only 47.1 μg/cm². The lens of composition 1C (1.8 g HEMA, 1.2 g VP, 0.09 g MAA, cross-linked with 0.06 g TEGDMA), when coated with a 1% solution of PEGDA 4000 showed an approximately 50% decrease in BSA absorption from 88.4 μg/cm² for control lens to 40.6 μg/cm² for the coated material.

EXAMPLE 10

Cross-Linking of Preformed Polymer

Cross-Linking of preformed polymer, a stock solution of 10 g polyvinyl pyrrolidone (PVP) of molecular weight 360,000 was dissolved in 100 ml ethyl alcohol. One drop of Durocure 1173 and 6.0–60% of cross-linker was added to each 10 ml aliquot. Films were cast from the solution, the solvent evaporated, and the films exposed to UV light for 30 seconds. The resulting lenses showed consistently high EWC values even in the pres-

TABLE 6

| Composition | % Cross-linker | EWC | Protein μg/cm² BSA | IgG | Lysozyme | Total |
|---|---|---|---|---|---|---|
| 1C | 2.3% TEGDMA | 52 | 88.4 | 3.69 | 380.7 | 472.8 |
| 28 | 20% PEGDA4000 | 64 | 39.7 | — | — | — |
| 29 | 2.5% HFPMBA | 53 | 52.4 | — | 344.0 | — |
| 30 | 24% PEGDA4000, 6% HFPMBA | 52 | 40.2 | 1.51 | 42.8 | 84.5 |

It is clear from the results in Table 6 that the correct combination of hydrophilic and hydrophobic cross-linking while maintaining the moisture content dramatically lowers the absorption of protein by a factor of 5–6.

Table 7 shows similar results with regard to altering the cross-linker from a hydrophilic conventional linker to a hydrophobic one in compositions containing elevated amounts of methylacrylic acid.

TABLE 7

| Composition | % Cross-linker | EWC | Protein μg/cm² BSA | IgG | Lysozyme | Total |
|---|---|---|---|---|---|---|
| 1D | 7% TEGDMA | 34 | 77.7 | 3.18 | 96.6 | 177.5 |
| 31 | 7% HFPMBA | 32 | 59.0 | 4.50 | 43.4 | 106.9 |

These compositions contained 1.80 g HEMA, 1.20 g VP, and 0.31 g of methylacrylic acid. Composition 1D, representing the prior art composition in Table 7, addience of 60% hydrophobic cross-linker. These results are shown in Table 8.

TABLE 8

| HFPMDA | TEGDMA | EWC |
|---|---|---|
| 0.06 | — | 89 |
| 0.11 | — | 91 |
| 0.24 | — | 79 |
| 0.60 | — | 76 |
| — | 0.06 | 95 |
| — | 0.11 | 93 |
| — | 0.26 | 91 |

TABLE 8-continued

| HFPMDA | TEGDMA | EWC |
|--------|--------|-----|
| —      | 0.60   | 85  |

The values in Table 8 represent grams of cross-linker per gram of PVP. Of course, as expected, slightly higher water absorption was obtained in the presence of the hydrophilic cross-linker TEGDMA.

EXAMPLE 11

Additional Compositions

Compositions were also prepared using the general technique described above with various ratios of VP to HEA in the basic polymer composition and approximately 20% HFPMDA or TEGDMA cross-linker. The water absorption appeared to reach a maximum at intermediate compositions of VP/HEA ratios whether hydrophilic or hydrophobic cross-linkers were used as shown in Table 9.

TABLE 9

| VP(g) | HEA(g) | Cross-Linker (g) | EWC |
|-------|--------|------------------|-----|
| 2.0   | —      | 0.40 HFPMDA      | 17  |
| 1.5   | 0.5    | "                | 36  |
| 1.0   | 1.0    | 0.44 HFPMDA      | 32  |
| 0.5   | 1.6    | 0.46 HFPMDA      | 27  |
| —     | 2.0    | 0.46 HFPMDA      | 26  |
| 2.0   | —      | 0.40 TEGDMA      | 36  |
| 1.5   | 0.5    | "                | 46  |
| 1.0   | 1.0    | "                | 45  |
| 0.5   | 1.5    | "                | 38  |
| —     | 2.0    | "                | 34  |

These results indicate water content to be relatively independent of basic polymer ratio (within the soft gel category) for a given cross-linker percentage. As expected, in additional experiments, compositions containing a constant ratio of HEA to VP (3:1) showed decreasing moisture contents as the percentage HFPMDA polymer was increased from 3% to 100% (from 59% EWC to and was less dramatically reduced (52% to 23%) when increasing percentages of TEGDMA from 6% to 90% were used. A large number of compositions containing various HEA/VP ratios and percentages of cross-linker were also prepared and found to have EWC values in the range of 40%–80% For example, compositions with HEA:VP of about 4:12 to 5:1 had EWC values of 71%–74%, despite the variation of PEGDA 4000 cross-linker from about 3% to about 60%. The EWC value was lowered slightly if HFPMDA with PEGDA 4000 was used as an additional cross-linker. EWC values of 73%–76% were also obtained when HEA:VP ratios of 4:1 containing approximately 12% PEGDA 4000 were supplemented with varying amounts (26%–100%) EEEA.

Use of a small molecular weight cross-linker such as HFPMDA or TEGDMA at approximately 20% resulted in somewhat lower EWC values (9%–40%), regardless of VP:HEMA ratio. These results were maintained over increasing levels of these low molecular weight cross-linkers. However, inclusion of 20% PEGDA as cross-linker in compositions having 4:1 HEMA:VP ratios permitted the addition of these same low molecular weight cross-linkers without substantial effect on moisture content.

EXAMPLE 12

In Situ Formation of Cross-Linker/Blends

Various compositions were also made using possible in situ formation of cross-linker from acrylic acid and polyethylene glycol. These compositions resulted in high quality lenses which were transparent and tough when saturated with water. Exemplary compositions contain 2.16 g HEA and 0.54 g VP as the basic polymerizing composition and 0.3 g of acrylic acid along with 0.03 g–0.40 g of polyethylene glycol, molecular weight 1500. Compositions containing ethoxyethoxyethyl acrylate (EEEA) in the basic polymer also gave satisfactory water contents when PEGDA 4000 was used as a cross-linker.

EXAMPLE 13

Polymeric Ester Copolymer

HEMA is used as the basic monomeric unit; the compositions use PEGMA of varying molecular weights with or without the monoesters of methacrylic acid with $HOCH_2(CF_2)_m CH_2OH$ (FAmMA) as copolymerizing units. Various compositions include 10%, 10% and 90% PEGMA 200, 10%, 30% and 90% PEGMA 4000, 10%, 30% and 90% PEGMA 10000, 10% PEGMA 400 with 20% $FA_8MA$, 30% PEGMA 1000 with 10% $FA_5MA$; and 80% PEGMA 600 with 10% $FA_3MA$.

EXAMPLE 14

In compositions similar to those of Example 12, blends are prepared using HEMA:VP, 4:1 as the basic polymer, and including 1%, 10%, or 40% PEG (MW 2000) or 2%, 5% or 30% of its dimethylether (MW 4000) in the mixture, along with appropriate amounts of MAA or AC. The compositions, of the following components, also exhibit satisfactory optical and protein resistance qualities.

TABLE 10

| Composition No. | Additives |
|-----------------|-----------|
| 1 | 1% PEG, 1% MAA |
| 2 | 10% PEG, 5% MAA |
| 3 | 40% PEG, 20% AC |
| 4 | 2% diether, 2% AC |
| 5 | 5% diether, 5% MAA |
| 6 | 30% diether, 17% MAA |
| 7 | 10% dieter, 10% MAA |
| 8 | 50% diether, 15% AC |
| 9 | 80% diether, 15% AC |

EXAMPLE 15

Compositions Containing Silyl Sidechains in the Backbone Monomer

The following mixtures were polymerized by mixing the monomers, degassing with nitrogen and polymerizing using UV light or heat depending on the catalyst used in the mixture. The polymerized mixtures can be formed into buttons and assessed for hardness and water content as described above.

Composition 1: Composition 1 was formed from 41 g TRIS; 20 g MMA; 20 g PEGMA 350; 9 g EGDMA; and 0.1 g of the photoiniator Durocure 1173. After degassing and polymerization with UV light, the buttons were machined into lenses which were transparent and showed a hardness of 82 and equilibrium water content of 3.2%. The lenses have a high oxygen permeability but the wettability is poor.

Composition 2: Composition 2 was formed from 49 g TRIS, 15 g isobornyl methacrylate (IBMA), 20 g PEGMA 2000, 10 g N-VP, 6 g EDGMA, in the presence of 0.004 g AIBN. Polymerization after degassing was at 60° for 12 hr resulting in a transparent material with a hardness of 83 and an equilibrium water content of 3.5%.

Composition 3: Composition 3 was prepared from 50 g TRIS, 10 g HFBMA, 36 g PEGMA 550, 4 g EGDMA in the presence of 0.005 g AIBN. Polymerization was at 60° for 15 hr and the resulting polymer composition showed a hardness of 84 and an equilibrium water content of 2.4%.

Composition 4: This composition was polymerized from 50 g TRIS, 10 g pentadecafluorooctylmethacrylate (PDFOMA), 30 g PEGMA (750), 10 g MMA, 10 g PEGDMA (1000) in the presence of 0.1 g Durocure 1173. Polymerization was by UV light to give a composition of hardness 84 and equilibrium water content of 2.2%.

Composition 5: A more hydrophilic composition was formed from 60 g tridecafluorooctylmethacrylate (TDFOMA), 40 g PEGMA 550, 0.5 g diethylene glycoldimethacrylate and 0.1 g of Durocure 1173. After degassing and polymerization by UV light, a composition of hardness 83 and an equilibrium water content of 25% was obtained.

Composition 6: Composition 6 again contains TRIS (50 g), 10 g MMA, 10 g BMA, 15 g PEGMA 350, 5 g NVP, and 6 g hexafluoropentamethylene dimethacrylate in the presence of 0.04 g AIBN. Polymerization at 45° for 24 hr resulted in a composition of hardness 84 and equilibrium water content 2%.

Composition 7: A highly fluorinated composition shows a low water content, this composition is formed from 26 g PDFOMA, 61 g HFBMA, 10 g PEGMA 350, 3 g EGDMA in the presence of 0.2 g Durocure 1173. After polymerization with UV light, the composition had a hardness of 70 and an equilibrium water content of 0.9%.

Compositions 8-10: Three additional compositions were prepared by degassing and polymerization with UV light. These were as follows:

Composition 8; 16 g PDFOA, 13 g HFBMA, 40 g TRIS, 25 g PEGMA 550, 6 g EGDMA and 0.2 Durocure;

Composition 9; 45.5 g HFBMA, 3.a3 g PEGMA 350, 25.2 g IBMA, 1.2 g EGDMA and 0.8 g Durocure 1173;

Composition 10; 30 g TRIS, 4.3 g PDFOA, 6.2 g NVP, 6.2 g PEGMA 350, 12.0 g MMA, 2.0 g hexanediol dimethacrylate (HDDMA), and 0.5 g Durocure 1173.

EXAMPLE 16

Preparation of a Siloxane-containing Cross-linker

A block copolymer of polydimethylsiloxane and polyethylene oxide (PDMS/PEO) was converted to a cross-linker by diesterification. The copolymer was dissolved in dry tetrahydrofuran and stoichiometric amounts of methacryloyl chloride and triethylamine were added dropwise with stirring. Reaction precipitates the hydrochloride of triethylamine, which was filtered off when reaction was complete. The resulting diester was washed with aqueous solution of sodium carbonate to remove any remaining acidic contaminants. The resulting diester can be used as an additional cross-linker in concert with the others used in the compositions of the invention.

EXAMPLE 17

Preparation of a Grafted Protein-resistant Surface

Tubing composed of polyethylene, polypropylene, silicone, polyurethane or polyvinyl chloride was swelled in the presence of a solvent containing 10% by weight of PEGMA 350/5% PEGDA 4000. The swollen tubing in the presence of the solution was exposed to high intensity UV light. The grafted tubing was then washed with pure solvent and then with methylene chloride and vacuum dried.

Assay for successful grafting was conducted by measurement of water spreading on the surface of the tubing. Successful grafts resulted in a more facile spread of water placed in contact with the tubing.

EXAMPLE 18

Protein Resistant Properties of Lenses Containing Backbone polymers Derived from PEG Monoesters of Unsaturated Carboxylic Acids The ability of lenses containing substantial amounts of the essential PEG component in the form of polymerized residues of PEG monoesters of unsaturated acids to resist protein but maintain a satisfactory water content (EWC) was compared to these properties of standard lenses. None of the test compositions contained free carboxylic acid components; in no cases were the lenses treated with alkali before testing for EWC. The lenses were prepared by polymerization as described hereinabove; protein content and EWC were determined as described in Examples 1 and 2.

A number of control and test compositions were prepared, all using polymerization with 0.8 g Durocure 1173 per 100 g of polymerizing backbone mixture under UV light to effect polymerization. The polymerized composition was then formed into lenses for testing of EWC and protein content. Where cross-linking is indicated, this was effected by the addition of 0.4 g ethylene glycol dimethacrylate (EGDMA) per 100 g of backbone polymer.

The control compositions contained standard monomer components, hydroxyethyl methacrylate (HEMA), N-vinyl pyrrolidone (VP) and methyl methacrylate (MMA). In one instance, the control composition contained methacrylic acid (MAA). The test compositions contained similar components (except that free carboxylic acid was never included). The test composition included, in addition, the polyethylene glycol-containing monomer, polyethylene glycol methacrylate (PEGMA, MW=350-5000). A comparison of the properties of the control and test compositions is shown in Table 11 below.

TABLE 11

| Composition | Backbone Composition | X-linked? | EWC | Lysosyme Absorbed (μg/lens) | Albumin Absorbed (μg/lens) |
|---|---|---|---|---|---|
| Control 1A | 30% HEMA 45% VP 25% MMA | yes | 55% | 196 | 14.5 |
| Test 1B | 30% HEMA 15% VP 25% MMA 30% PEGMA (350) | yes | 55% | 34 | 10 |
| Test 2B | 45% HEMA 5% VP | yes | 55% | 20 | 6 |

TABLE 11-continued

| Composition | Backbone Composition | X-linked? | EWC | Lysosyme Absorbed (μg/lens) | Albumin Absorbed (μg/lens) |
|---|---|---|---|---|---|
| | 20% MMA 30% PEGMA (750) | | | | |
| Control 3A | 74% VP 26% MMA | yes | 74% | 157 | 16 |
| Test 3B | 45% VP 25% MMA 30% PEGMA (2000) | yes | 74% | 56 | 14 |
| Control 4A | 97.5% HEMA 2.5% MAA | no | 55% | 510 | 7 |
| Test 4B | 31% HEMA 69% PEGMA (5000) | no | 65% | 30 | 8 |

As shown in Table 11, all test compositions had much lower absorptions of protein, particularly lysozyme, than did the corresponding controls, although the water contents of all compositions were similar. It is to be noted, in particular, that the inclusion of a small amount of free carboxylic acid dramatically increases the lysozime absorption. Accordingly, the lenses of the compositions containing PEG monomers specifically do not include free carboxylic acids.

I claim:

1. A protein-resistant medical device constructed of a composition comprising a copolymer which includes 1-69% of at least one unsaturated monoester of a polyethylene glycol of the formula $HO(CH_2CH_2O)_nR$, wherein n is 8-300 and wherein R is H or lower alkyl (1-4C).

2. The medical device of claim 1, wherein up to 90% of the unsaturated monoester of said polyethylene glycol is replaced by an unsaturated monoester of an alcohol of the formula $HO(CH_2)_l(CF_2)_mCF_3$ wherein l is 1-5 and m is 1-10.

3. A protein-resistant medical device constructed of a composition comprising a copolymer which includes 1-90% of at least one unsaturated monoester of a polyethylene glycol of the formula $HO(CH_2CH_2O)_nR$, wherein n is 8-300, and wherein R is H, lower alkyl or saturated acyl, wherein said composition can absorb more than 40% water content and said composition is not treated with alkali.

4. A protein-resistant medical device constructed of a composition comprising a copolymer which includes 1-90% of at least one unsaturated monoester of a polyethylene glycol of the formula $HO(CH_2CH_2O)_nR$, wherein n is 8-300, and wherein R is H, lower alkyl or saturated acyl, wherein said composition does not contain free carboxylic acid.

5. The medical device of claims 3-6 wherein the polymer of copolymer is formed from one or more monomers selected from the group consisting of unsaturated carboxylic acids and their hydrocarbyl, hydroxylated hydrocarbl, silylated, and fluorinated ester and vinyl derivatives.

6. The medical device of claim 7 wherein the unsaturated carboxylic acids and esters are selected for HEA, HEMA, MAA, AC, FA, FMA, DHPM, MMA, GMA, AA, HFBMA, IBMA, PDFORMA, TDFOMA, and TRIS, and the vinyl derivative is VP.

7. The medical device of claims 3-6 which is a contact lens.

8. A protein-resistant medical device constructed of a composition consisting essentially of a polymer or copolymer
cross-linked with a relative percent of 0.1-90% of the unsaturated diester form of at least one diol selected from the group consisting of:
(a) at least one polydimethyl siloxane/polyethlene glycol copolymer (PMS/PEG) of the formula $HO(Si(Me_2O))_x$—$(CH_2CH_2O)_yH$ wherein x is 1-300 and y is 1-400;
(b) a mixture of said PMS/PEG with at least one fluoromethylene diol (FMD) of the formula $HO(CH_2(CF_2)_mCH_2OH$ wherein m is 1-10;
(c) a mixture of said PMS/PEG with at least one polyethylene glycol (PEG) of the formula $HO(CH_2CH_2O)_nH$ wherein n is 1-300; and
(d) a mixture of said PMS/PEG with a mixture of said FMD and PEG.

* * * * *